(12) United States Patent
Bryan et al.

(10) Patent No.: US 7,700,103 B2
(45) Date of Patent: Apr. 20, 2010

(54) OPTIMIZED EXPRESSION OF HPV 52 L1 IN YEAST

(75) Inventors: Janine T. Bryan, Furlong, PA (US); Michelle K. Brownlow, Jamison, PA (US); Loren D. Schultz, Harleysville, PA (US); Kathrin U. Jansen, South San Francisco, CA (US)

(73) Assignee: Merck & Co., Inc., Rahway, NJ (US)

( * ) Notice: Subject to any disclaimer, the term of this patent is extended or adjusted under 35 U.S.C. 154(b) by 586 days.

(21) Appl. No.: 10/594,064

(22) PCT Filed: Mar. 18, 2005

(86) PCT No.: PCT/US2005/009199
§ 371 (c)(1),
(2), (4) Date: Sep. 25, 2006

(87) PCT Pub. No.: WO2005/097821
PCT Pub. Date: Oct. 20, 2005

(65) Prior Publication Data
US 2008/0226660 A1  Sep. 18, 2008

Related U.S. Application Data

(60) Provisional application No. 60/555,926, filed on Mar. 24, 2004.

(51) Int. Cl.
*A61K 39/00* (2006.01)
*C07H 21/04* (2006.01)
*C12N 15/00* (2006.01)

(52) U.S. Cl. ............... 424/184.1; 435/320.1; 435/255.1; 435/69.1

(58) Field of Classification Search .................. None
See application file for complete search history.

(56) References Cited

U.S. PATENT DOCUMENTS

| | | | |
|---|---|---|---|
| 5,643,715 A * | 7/1997 | Lancaster | 435/5 |
| 5,821,087 A | 10/1998 | Lowe et al. | |
| 6,159,729 A | 12/2000 | Hofmann et al. | |
| 7,276,243 B2 * | 10/2007 | Jansen et al. | 424/204.1 |

FOREIGN PATENT DOCUMENTS

| | | |
|---|---|---|
| WO | WO 98/34640 | 8/1998 |
| WO | WO 99/02694 | 1/1999 |
| WO | WO 00/09157 | 2/2000 |
| WO | WO 01/14416 A2 | 3/2001 |
| WO | WO 02/08435 A1 | 1/2002 |
| WO | WO 2004/084831 A2 | 10/2004 |
| WO | WO 2005/032586 | 4/2005 |
| WO | WO 2005/047315 | 5/2005 |

OTHER PUBLICATIONS

Hoffman et al., "Sequence determination of Human papillomavirus type 6a and assembly of virus-like particles in *Saccharomyces cerevisiae*", Virology 209, 506-518, 1995.*
Sharp et al. "Synonymous codon usage in *Saccharomyces cerevisiae*", Yeast vol. 7: 657-678 (1991).*
Neeper et al., "Expression of the major capsid protein of human papillomavirus type 11 in *Saccharomyces cerevisae*", Gene 180 (1996) 1-6.*
GenBank Accession No. M96297, Aug. 2, 1993.
Bosch, et al., "The casual relation between human papillomavirus and cervical cancer", J. Clin. Path., vol. 55, pp. 244-265, 2002.
Breitburd, et al., "Immunization with Viruslike Particles from Cottontail Rabbit Papillomavirus (CRPV) Can Protect against Experimental CRPV Infection", J. of Virol., vol. 69, No. 6, Jun. 1995, pp. 3959-3963.
Chan, et al., "Phylogenetic Analysis of 48 Papillomavirus Types and 28 Subtypes and Variants: a Showcase for the Molecular Evolution of DNA Viruses", Journal of Virology, vol. 66, No. 10, pp. 5714-5725, 1992.
Database Accession No. Q05138.
GenBank Accession No. #NC 001592.
Guo, et al., "Signals Sufficient for 3'-End Formation of Yeast mRNA", Mol and Cell Biology, vol. 16, No. 6, pp. 2772-2776, Jun. 1996.
Guo, et al., "3'-end-forming signals of yeast mRNA", TIBS 21, pp. 477-481.
Heidmann, et al., "Flexibility and Interchangeability of Polyadenylation Signals in *Saccharomyces cerevisiae*", Mol. And Cell Biology, vol. 14, No. 7, 1994, pp. 4633-4642.

(Continued)

*Primary Examiner*—Andrew Wang
*Assistant Examiner*—Kagnew H Gebreyesus
(74) *Attorney, Agent, or Firm*—Alysia A. Finnegan; Sheldon O. Heber

(57) ABSTRACT

Synthetic DNA molecules encoding the HPV 52 L1 protein are provided. Specifically, the present invention provides polynucleotides encoding HPV 52 L1 protein, wherein said polynucleotides are codon-optimized for high level expression in a yeast cell. In alternative embodiments of the invention, the nucleotide sequence of the synthetic molecule is altered to eliminate transcription termination signals that are recognized by yeast. The synthetic molecules may be used to produce HPV 52 virus-like particles (VLPs), and to produce vaccines and pharmaceutical compositions comprising the HPV 52 VLPs. The vaccines of the present invention provide effective immunoprophylaxis against papillomavirus infection through neutralizing antibody and cell-mediated immunity and may also be useful for treatment of existing HPV infections.

7 Claims, 9 Drawing Sheets

OTHER PUBLICATIONS

Henikoff, et al., "Transcription Terminates in Yeast Distal to a Control Sequence", Cell., vol. 33, Jun. 1983, pp. 607-614.

Hofmann, et al., "Sequence Determination of Human Papillomavirus Type 6a and Assembly of Virus-Like Particles in *Saccharomyces cerevisiae*", Virology, vol. 209, 1995. pp. 506-518.

Jansen, et al., "Vaccination with yeast-expressed cottontail rabbit papillomavirus (CRPV) virus-like particles protects rabbits from CRPV-induced papillomavirus formation", Vaccine, vol. 13, No. 16, 1995, pp. 1509-1514.

Kotula, et al., "Evaluation of Foreign Gene Codon Optimization in Yeast: Expression of a Mouse IG Kappa Chain", Biotechnology, vol. 9, Dec. 1991, pp. 1386-1389.

Liu, et al., "Polynucleotide viral vaccines: codon optimisation and ubiquitin conjugation enhanced prophylactic and therapeutic efficacy", Vaccine, vol. 20, No. 5-6, 2002, pp. 862-869.

McMurray, et al., "Biology of human papillomaviruses", J. Exp. Path., vol. 82, 2001, pp. 15-33.

Neeper, et al., "Expression of the major capsid protein of human papillomavirus type 1 in *Saccharomyces cerevisae*", Gene, vol. 180, No. 1-2, pp. 1-6, 1996.

Russo, et al., "*Saccharomyces cerevisiae* mRNA 3' End Forming Signals are also Involved in Transcription Termination", Yeast, vol. 11, 1995, pp. 447-453.

Schiffman, et al., "Epidemiologic Evidence Showing That Human Papillomavirus Infection Causes Most Cervical Intraepithelial Neoplasia", J. of National Cancer Inst., vol. 85, vol. 12, 1993, pp. 958-964.

Schiller, et al., "Papillomavirus-Like Particles: Basic and Applied Studies", UK: Leeds Medical Information, 1996, pp. 101-112.

Schiller, et al., "Papillomavirus-Like Particle Vaccines", J. Natl. Cancer Inst. Monographs, No. 28, 2000, pp. 50-54.

Schiller, et al., "Developing HPV virus-like particle vaccines to prevent cervical cancer: a progress report", J. of Clin. Virology., vol. 19, 2000, pp. 67-74.

Sharp, et al., "Synonymous Codon Usage in *Saccharomyces cerevisiae*", Yeast, vol. 7, 1991, pp. 657-678.

Suzich, et al., "Systemic immunization with papillomavirus L1 protein completely prevents the development of viral mucosal papillomas", PNAS USA, vol. 92, Dec. 1995, pp. 11553-11557.

Thalenfeld, et al., "oli 1 Transcripts in Wild Type and in a Cytophasmic 'Petite' Mutant of Yeast", J. of Biol Chem., vol. 258, No. 23, Dec. 10, 1983, pp. 14065-14065.

Tobery, et al., "Effect of vaccine delivery system on the induction of HPV 16L1-specific humoral and cell-mediated immune responses in immunized rhesus macaques", Vaccine, vol. 21, 2003, pp. 1539-1547.

Zaret, et al., "DNA Sequence Required for Efficient Transcription Termination in Yeast", Cell, vol. 28, Mar. 1982, pp. 563-573.

Zaret, et al., "Mutationally Altered 3' Ends of Yeast CYC1 mRNA Affect Transcript Stability and Translational Efficiency", J. Mol. Biol., vol. 176, 1984, pp. 107-135.

Zhou, et al., "Papillomavirus Capsid Protein Expression Level Depends on the Match Between Codon Usage and tRNA Availability", J. of Virol., vol. 73, No. 6, Jun. 1999, pp. 4972-4982.

* cited by examiner

HPV 52 L1 Nucleotide Sequence Alignment

| | | |
|---|---|---|
| 52 L1 wt | ( 1) | ATGTCCGTGTGGCGGCCTAGTGAGGCCACTGTGTACCTGCCTCCTGTACC |
| 52 L1 R | | ........C...A.A..ATCC..A..T....C...T....A..A...T.. |
| 52 L1 wt | ( 51) | TGTCTCTAAGGTTGTAAGCACTGATGAGTATGTGTCTCGCACAAGCATCT |
| 52 L1 R | | A............CTCT..C..C..A..C..C..CA.A..CTC....... |
| 52 L1 wt | ( 101) | ATTATTATGCAGGCAGTTCTCGATTACTAACAGTAGGACATCCCTATTTT |
| 52 L1 R | | .C..C..C..T..TTCC...A....GT.G..T..C..T..C..A..C..C |
| 52 L1 wt | ( 151) | TCTATTAAAAACACCAGTAGTGGTAATGGTAAAAAAGTTTTAGTTCCCAA |
| 52 L1 R | | .....C..G......TCCTCC.....C.....G..G..C..G.....A.. |
| 52 L1 wt | ( 201) | GGTGTCTGGCCTGCAATACAGGGTATTTAGAATTAAATTGCCGGACCCTA |
| 52 L1 R | | ...C.....TT..........A..C..C.....C..G.....A.....A. |
| 52 L1 wt | ( 251) | ATAAATTTGGTTTTCCAGATACATCTTTTTATAACCCAGAAACCCAAAGG |
| 52 L1 R | | .C..G..C.....C.....C..TAG...C..C...........T.....A |
| 52 L1 wt | ( 301) | TTGGTGTGGGCCTGTACAGGCTTGGAAATTGGTAGGGGACAGCCTTTAGG |
| 52 L1 R | | .....C.....T.....T..T........C.....A..T..A..A..G.. |
| 52 L1 wt | ( 351) | TGTGGGTATTAGTGGGCATCCTTTATTAAACAAGTTTGATGATACTGAAA |
| 52 L1 R | | ...C.....CTC...T..C..A..G..G........C..C..C....... |
| 52 L1 wt | ( 401) | CCAGTAACAAATATGCTGGTAAACCTGGTATAGATAATAGGGAATGTTTA |
| 52 L1 R | | ..TC......G..C........G..A.....C.....C..A........G |
| 52 L1 wt | ( 451) | TCTATGGATTATAAGCAGACTCAGTTATGCATTTTAGGATGCAAACCTCC |
| 52 L1 R | | ........C..C.....A.....A..G..T..C..G..T..T..G..A.. |
| 52 L1 wt | ( 501) | TATAGGTGAACATTGGGGTAAGGGAACCCCTTGTAATAATAATTCAGGAA |
| 52 L1 R | | A..C........C...........T..T..A.....C..C..C..T..T. |
| 52 L1 wt | ( 551) | ATCCTGGGGATTGTCCTCCCCTACAGCTCATTAACAGTGTAATACAGGAT |
| 52 L1 R | | .C..A..T..C.....A..AT.G..AT.G..C...TCC..C..C..A..C |
| 52 L1 wt | ( 601) | GGGGACATGGTAGATACAGGATTTGGTTGCATGGATTTTAATACCTTGCA |
| 52 L1 R | | ..T........C..C..T..T..C.....T.....C..C..C........ |

FIG.1A

```
52 L1 wt   ( 651)  AGCTAGTAAAAGTGATGTGCCCATTGATATATGTAGCAGTGTATGTAAGT
52 L1 R            ....TC...GTCC..C..C..A..C..C..C...TC.TC... C.......

52 L1 wt   ( 701)  ATCCAGATTATTTGCAAATGGCTAGCGAGCCATATGGTGACAGTTTGTTC
52 L1 R            .C.....C..C...........TCT..A.....C......TCC......

52 L1 wt   ( 751)  TTTTTTCTTAGACGTGAGCAAATGTTTGTTAGACACTTTTTTAATAGGGC
52 L1 R            ..C..CT.G...A.A..A........C..C........C..C..C..A..

52 L1 wt   ( 801)  CGGTACCTTAGGTGACCCTGTGCCAGGTGATTTATATATACAAGGGTCTA
52 L1 R            T........G........A..T........C..G..C..C.. ...T..C.

52 L1 wt   ( 851)  ACTCTGGCAATACTGCCACTGTACAAAGCAGTGCTTTTTTTCCTACTCCT
52 L1 R            .......T..C.....T.....C...TC.TC......C..C. .A.....A

52 L1 wt   ( 901)  AGTGGTTCTATGGTAACCTCAGAATCCCAATTATTTAATAAACCGTACTG
52 L1 R            TC......C.....C.....C.........G..C..C..G ..A.....

52 L1 wt   ( 951)  GTTACAACGTGCGCAGGGCCACAATAATGGCATATGTTGGGGCAATCAGT
52 L1 R            ...G...A.A..T..A..T.....C..C..T..C........T..C..A.

52 L1 wt   (1001)  TGTTTGTCACAGTTGTGGATACCACTCGTAGCACTAACATGACTTTATGT
52 L1 R            ....C.....C..C..C.,C..T...A.ATCT.......... .C..G...

52 L1 wt   (1051)  GCTGAGGTTAAAAAGGAAAGCACATATAAAAATGAAAATTTTAAGGAATA
52 L1 R            .....A..C..G......TC...C..C..G..C.....C..C........

52 L1 wt   (1101)  CCTTCGTCATGGCGAGGAATTTGATTTACAATTTATTTTTCAATTGTGCA
52 L1 R            .T.GA.A..C..T..A.....C..C..G.....C..C..C.. .......T.

52 L1 wt   (1151)  AAATTACATTAACAGCTGATGTTATGACATACATTCATAAGATGGATGCC
52 L1 R            .G..C..C..G..C.....C..C.....T.....C..C.... .....C..T

52 L1 wt   (1201)  ACTATTTTAGAGGACTGGCAATTTGGCCTTACCCCACCACCGTCTGCATC
52 L1 R            .....C..G..A...........C...TT.G..T........A ..C..T..

52 L1 wt   (1251)  TTTGGAGGACACATACAGATTTGTCACTTCTACTGCTATAACTTGTCAAA
52 L1 R            C.....A.....T........C........C.........C..C......
```

FIG. 1B

```
52 L1 wt    (1301)    AAAACACGCCACCTAAAGGAAAGGAAGATCCTTTAAAGGACTATATGTTT
52 L1 R               .G.....T.....A..G..T........C..A..G......C... ...C

52 L1 wt    (1351)    TGGGAGGTGGATTTAAAAGAAAAGTTTTCTGCAGATTTAGATCAGTTTCC
52 L1 R               .....A..C..C..G..G........C.....T..C..G..C..A..C..

52 L1 wt    (1401)    TTTAGGTAGGAAGTTTTTGTTACAGGCAGGGCTACAGGCTAGGCCCAAAC
52 L1 R               A..G.....A.....C.....G..A..T..TT.G..A.....A...A..GT

52 L1 wt    (1451)    TAAAACGCCCTGCATCATCGGCCCCACGTACCTCCACAAAGAAGAAAAAG
52 L1 R               .G..GA.A..A..TAGC..T..T...A.A..T.....C........G...

52 L1 wt    (1501)    GTTAAAAGGTAA (SEQ ID NO:3)
52 L1 R               ..C..G..A...(SEQ ID NO:1)
```

FIG.1C

HPV 52 L1 R Nucleotide and Amino Acid Sequences

```
          M   S   V   W   R   P   S   E   A   T   V   Y   L   P   P   V   P
  1   ATGTCCGTCT GGAGACCATC CGAAGCTACT GTCTACTTGC CACCAGTTCC
      TACAGGCAGA CCTCTGGTAG GCTTCGATGA CAGATGAACG GTGGTCAAGG
          G   S   K   V   V   S   T   D   E   Y   V   S   R   T   S   I   Y
 51   AGTCTCTAAG GTTGTCTCTA CCGACGAATA CGTCTCCAGA ACCTCCATCT
      TCAGAGATTC CAACAGAGAT GGCTGCTTAT GCAGAGGTCT TGGAGGTAGA
          Y   Y   A   G   S   S   R   L   L   T   V   G   H   P   Y   F
101   ACTACTACGC TGGTTCCTCT AGATTGTTGA CTGTCGGTCA CCCATACTTC
      TGATGATGCG ACCAAGGAGA TCTAACAACT GACAGCCAGT GGGTATGAAG
          S   I   K   N   T   S   S   G   N   G   K   K   V   L   V   P   K
151   TCTATCAAGA ACACCTCCTC CGGTAACGGT AAGAAGGTCT TGGTTCCAAA
      AGATAGTTCT TGTGGAGGAG GCCATTGCCA TTCTTCCAGA ACCAAGGTTT
          V   S   G   L   Q   Y   R   V   F   R   I   K   L   P   D   P   N
201   GGTCTCTGGT TTGCAATACA GAGTCTTCAG AATCAAGTTG CCAGACCCAA
      CCAGAGACCA AACGTTATGT CTCAGAAGTC TTAGTTCAAC GGTCTGGGTT
          K   F   G   F   P   D   T   S   F   Y   N   P   E   T   Q   R
251   ACAAGTTCGG TTTCCCAGAC ACTAGTTTCT ACAACCCAGA AACTCAAAGA
      TGTTCAAGCC AAAGGGTCTG TGATCAAAGA TGTTGGGTCT TTGAGTTTCT
          L   V   W   A   C   T   G   L   E   I   G   R   G   Q   P   L   G
301   TTGGTCTGGG CTTGTACTGG TTTGGAAATC GGTAGAGGTC AACCATTGGG
      AACCAGACCC GAACATGACC AAACCTTTAG CCATCTCCAG TTGGTAACCC
          V   G   I   S   G   H   P   L   L   N   K   F   D   D   T   E   T
351   TGTCGGTATC TCTGGTCACC CATTGTTGAA CAAGTTCGAC GACACTGAAA
      ACAGCCATAG AGACCAGTGG GTAACAACTT GTTCAAGCTG CTGTGACTTT
          S   N   K   Y   A   G   K   P   G   I   D   N   R   E   C   L
401   CCTCTAACAA GTACGCTGGT AAGCCAGGTA TCGATAACAG AGAATGTTTG
      GGAGATTGTT CATGCGACCA TTCGGTCCAT AGCTATTGTC TCTTACAAAC
          S   M   D   Y   K   Q   T   Q   L   C   I   L   G   C   K   P   P
451   TCTATGGACT ACAAGCAAAC TCAATTGTGT ATCTTGGGTT GTAAGCCACC
      AGATACCTGA TGTTCGTTTG AGTTAACACA TAGAACCCAA CATTCGGTGG
          I   G   E   H   W   G   K   G   T   P   C   N   N   N   S   G   N
501   AATCGGTGAA CACTGGGGTA AGGGTACTCC ATGTAACAAC AACTCTGGTA
      TTAGCCACTT GTGACCCCAT TCCCATGAGG TACATTGTTG TTGAGACCAT
          P   G   D   C   P   P   L   Q   L   I   N   S   V   I   Q   D
551   ACCCAGGTGA CTGTCCACCA TTGCAATTGA TCAACTCCGT CATCCAAGAC
      TGGGTCCACT GACAGGTGGT AACGTTAACT AGTTGAGGCA GTAGGTTCTG
          G   D   M   V   D   T   G   F   G   C   M   D   F   N   T   L   Q
601   GGTGACATGG TCGACACTGG TTTCGGTTGT ATGGACTTCA ACACCTTGCA
      CCACTGTACC AGCTGTGACC AAAGCCAACA TACCTGAAGT TGTGGAACGT
```

FIG.2A

```
         A   S   K       S   D   V   P       I   D   I       C   S   S       V   C   K   Y
 651   AGCTTCTAAG  TCCGACGTCC  CAATCGACAT  CTGTTCCTCT  GTCTGTAAGT
       TCGAAGATTC  AGGCTGCAGG  GTTAGCTGTA  GACAAGGAGA  CAGACATTCA
           P   D   Y       L   Q   M       A   S   E   P       Y   G   D       S   L   F
 701   ACCCAGACTA  CTTGCAAATG  GCTTCTGAAC  CATACGGTGA  CTCCTTGTTC
       TGGGTCTGAT  GAACGTTTAC  CGAAGACTTG  GTATGCCACT  GAGGAACAAG
         F   F   L   R       R   E   Q       M   F   V       R   H   F   F       N   R   A
 751   TTCTTCTTGA  GAAGAGAACA  AATGTTCGTC  AGACACTTCT  TCAACAGAGC
       AAGAAGAACT  CTTCTCTTGT  TTACAAGCAG  TCTGTGAAGA  AGTTGTCTCG
           G   T   L       G   D   P   V       P   G   D       L   Y   I       Q   G   S   N
 801   TGGTACCTTG  GGTGACCCAG  TTCCAGGTGA  CTTGTACATC  CAAGGTTCCA
       ACCATGGAAC  CCACTGGGTC  AAGGTCCACT  GAACATGTAG  GTTCCAAGGT
           S   G   N       T   A   T       V   Q   S   S       A   F   F       P   T   P
 851   ACTCTGGTAA  CACTGCTACT  GTCCAATCCT  CTGCTTTCTT  CCCAACTCCA
       TGAGACCATT  GTGACGATGA  CAGGTTAGGA  GACGAAAGAA  GGGTTGAGGT
         S   G   S   M       V   T   S       E   S   Q       L   F   N   K       P   Y   W
 901   TCTGGTTCCA  TGGTCACCTC  CGAATCCCAA  TTGTTCAACA  AGCCATACTG
       AGACCAAGGT  ACCAGTGGAG  GCTTAGGGTT  AACAAGTTGT  TCGGTATGAC
           L   Q   R       A   Q   G   H       N   N   G       I   C   W       G   N   Q   L
 951   GTTGCAAAGA  GCTCAAGGTC  ACAACAACGG  TATCTGTTGG  GGTAACCAAT
       CAACGTTTCT  CGAGTTCCAG  TGTTGTTGCC  ATAGACAACC  CCATTGGTTA
           F   V   T       V   V   D       T   T   R   S       T   N   M       T   L   C
1001   TGTTCGTCAC  CGTCGTCGAC  ACTACTAGAT  CTACTAACAT  GACCTTGTGT
       ACAAGCAGTG  GCAGCAGCTG  TGATGATCTA  GATGATTGTA  CTGGAACACA
           A   E   V   K       K   E   S       T   Y   K       N   E   N   F       K   E   Y
1051   GCTGAAGTCA  AGAAGGAATC  CACCTACAAG  AACGAAAACT  TCAAGGAATA
       CGACTTCAGT  TCTTCCTTAG  GTGGATGTTC  TTGCTTTTGA  AGTTCCTTAT
           L   R   H       G   E   E   F       D   L   Q       F   I   F       Q   L   C   K
1101   CTTGAGACAC  GGTGAAGAAT  TCGACTTGCA  ATTCATCTTC  CAATTGTGTA
       GAACTCTGTG  CCACTTCTTA  AGCTGAACGT  TAAGTAGAAG  GTTAACACAT
           I   T   L       T   A   D       V   M   T   Y       I   H   K       M   D   A
1151   AGATCACCTT  GACCGCTGAC  GTCATGACTT  ACATCCACAA  GATGGACGCT
       TCTAGTGGAA  CTGGCGACTG  CAGTACTGAA  TGTAGGTGTT  CTACCTGCGA
           T   I   L   E       D   W   Q       F   G   L       T   P   P   P       S   A   S
1201   ACTATCTTGG  AAGACTGGCA  ATTCGGTTTG  ACTCCACCAC  CATCCGCTTC
       TGATAGAACC  TTCTGACCGT  TAAGCCAAAC  TGAGGTGGTG  GTAGGCGAAG
           L   E   D       T   Y   R   F       V   T   S       T   A   I       T   C   Q   K
1251   CTTGGAAGAC  ACTTACAGAT  TCGTCACTTC  CACTGCTATC  ACCTGTCAAA
       GAACCTTCTG  TGAATGTCTA  AGCAGTGAAG  GTGACGATAG  TGGACAGTTT
```

FIG.2B

```
           N   T   P     P   K   G     K   E   D     P   L   K   D     Y   M   F
1301    AGAACACTCC  ACCAAAGGGT  AAGGAAGACC  CATTGAAGGA  CTACATGTTC
        TCTTGTGAGG  TGGTTTCCCA  TTCCTTCTGG  GTAACTTCCT  GATGTACAAG
           W   E   V   D     L   K   E     K   F   S     A   D   L   D     Q   F   P
1351    TGGGAAGTCG  ACTTGAAGGA  AAAGTTCTCT  GCTGACTTGG  ACCAATTCCC
        ACCCTTCAGC  TGAACTTCCT  TTTCAAGAGA  CGACTGAACC  TGGTTAAGGG
           L   G   R     K   F   L   L     Q   A   G     L   Q   A     R   P   K   L
1401    ATTGGGTAGA  AAGTTCTTGT  TGCAAGCTGG  TTTGCAAGCT  AGACCAAAGT
        TAACCCATCT  TTCAAGAACA  ACGTTCGACC  AAACGTTCGA  TCTGGTTTCA
             K   R   P     A   S   S     A   P   R   T     S   T   K     K   K   K
1451    TGAAGAGACC  AGCTAGCTCT  GCTCCAAGAA  CTTCCACCAA  GAAGAAGAAG
        ACTTCTCTGG  TCGATCGAGA  CGAGGTTCTT  GAAGGTGGTT  CTTCTTCTTC
         V   K   R   *   (SEQ ID NO:2)
1501    GTCAAGAGAT  AA (SEQ ID NO:1)
        CAGTTCTCTA  TT (SEQ ID NO:7)
```

FIG.2C

Transmission EM of VLPs Composed of HPV 52 L1 R Protein Molecules

US 7,700,103 B2

SEQUENCE LISTING

```
<160> NUMBER OF SEQ ID NOS: 7

<210> SEQ ID NO 1
<211> LENGTH: 1512
<212> TYPE: DNA
<213> ORGANISM: Artificial Sequence
<220> FEATURE:
<223> OTHER INFORMATION: HPV52L1R

<400> SEQUENCE: 1
atgtccgtct ggagaccatc cgaagctact gtctacttgc caccagttcc agtctctaag      60
gttgtctcta ccgacgaata cgtctccaga acctccatct actactacgc tggttcctct     120
agattgttga ctgtcggtca cccatacttc tctatcaaga cacctcctc cggtaacggt      180 aagaaggtct tggttccaaa ggtctctggt ttgcaataca gagtcttcag aatcaagttg     240
ccagacccaa acaagttcgg tttcccagac actagtttct acaacccaga aactcaaaga     300
ttggtctggg cttgtactgg tttggaaatc ggtagaggtc aaccattggg tgtcggtatc     360
tctggtcacc cattgttgaa caagttcgac gacactgaaa cctctaacaa gtacgctggt     420
aagccaggta tcgataacag agaatgtttg tctatggact acaagcaaac tcaattgtgt     480
atcttgggtt gtaagccacc aatcggtgaa cactggggta agggtactcc atgtaacaac     540
aactctggta acccaggtga ctgtccacca ttgcaattga tcaactccgt catccaagac     600
ggtgacatgg tcgacactgg tttcggttgt atggacttca acaccttgca agcttctaag     660
tccgacgtcc aatcgacat ctgttcctct gtctgtaagt acccagacta cttgcaaatg     720
gcttctgaac catacggtga ctccttgttc ttcttcttga agagaaca aatgttcgtc     780 agacacttct tcaacagagc tggtaccttg ggtgacccag ttccaggtga cttgtacatc     840
caaggttcca actctggtaa cactgctact gtccaatcct ctgctttctt cccaactcca     900
tctggttcca tggtcacctc cgaatcccaa ttgttcaaca agccatactg gttgcaaaga     960
gctcaaggtc acaacaacgg tatctgttgg ggtaaccaat tgttcgtcac cgtcgtcgac    1020
actactagat ctactaacat gaccttgtgt gctgaagtca gaaggaatc cacctacaag    1080 aacgaaaact tcaaggaata cttgagacac ggtgaagaat tcgacttgca attcatcttc    1140
caattgtgta gatcaccttt gaccgctgac gtcatgactt acatccacaa gatggacgct    1200
actatcttgg aagactggca attcggtttg actccaccac catccgcttc cttggaagac    1260
acttacagat tcgtcacttc cactgctatc acctgtcaaa agaacactcc accaaagggt    1320
aaggaagacc cattgaagga ctacatgttc tgggaagtcg acttgaagga aaagttctct    1380
```

-continued

```
gctgacttgg accaattccc attgggtaga aagttcttgt tgcaagctgg tttgcaagct    1440
agaccaaagt tgaagagacc agctagctct gctccaagaa cttccaccaa gaagaagaag    1500
gtcaagagat aa                                                        1512
```

<210> SEQ ID NO 2
<211> LENGTH: 503
<212> TYPE: PRT
<213> ORGANISM: Human papillomavirus type 52

<400> SEQUENCE: 2

```
Met Ser Val Trp Arg Pro Ser Glu Ala Thr Val Tyr Leu Pro Pro Val
 1               5                  10                  15

Pro Gly Ser Lys Val Val Ser Thr Asp Glu Tyr Val Ser Arg Thr Ser
                20                  25                  30

Ile Tyr Tyr Tyr Ala Gly Ser Ser Arg Leu Leu Thr Val Gly His Pro
            35                  40                  45

Tyr Phe Ser Ile Lys Asn Thr Ser Ser Gly Asn Gly Lys Lys Val Leu
        50                  55                  60

Val Pro Lys Val Ser Gly Leu Gln Tyr Arg Val Phe Arg Ile Lys Leu
65                  70                  75                  80

Pro Asp Pro Asn Lys Phe Gly Phe Pro Asp Thr Ser Phe Tyr Asn Pro
                85                  90                  95

Glu Thr Gln Arg Leu Val Trp Ala Cys Thr Gly Leu Glu Ile Gly Arg
            100                 105                 110

Gly Gln Pro Leu Gly Val Gly Ile Ser Gly His Pro Leu Leu Asn Lys
        115                 120                 125

Phe Asp Asp Thr Glu Thr Ser Asn Lys Tyr Ala Gly Lys Pro Gly Ile
    130                 135                 140

Asp Asn Arg Glu Cys Leu Ser Met Asp Tyr Lys Gln Thr Gln Leu Cys
145                 150                 155                 160

Ile Leu Gly Cys Lys Pro Pro Ile Gly Glu His Trp Gly Lys Gly Thr
                165                 170                 175

Pro Cys Asn Asn Asn Ser Gly Asn Pro Gly Asp Cys Pro Pro Leu Gln
            180                 185                 190

Leu Ile Asn Ser Val Ile Gln Asp Gly Asp Met Val Asp Thr Gly Phe
        195                 200                 205

Gly Cys Met Asp Phe Asn Thr Leu Gln Ala Ser Lys Ser Asp Val Pro
    210                 215                 220

Ile Asp Ile Cys Ser Ser Val Cys Lys Tyr Pro Asp Tyr Leu Gln Met
225                 230                 235                 240

Ala Ser Glu Pro Tyr Gly Asp Ser Leu Phe Phe Phe Leu Arg Arg Glu
                245                 250                 255

Gln Met Phe Val Arg His Phe Phe Asn Arg Ala Gly Thr Leu Gly Asp
            260                 265                 270

Pro Val Pro Gly Asp Leu Tyr Ile Gln Gly Ser Asn Ser Gly Asn Thr
        275                 280                 285

Ala Thr Val Gln Ser Ser Ala Phe Phe Pro Thr Pro Ser Gly Ser Met
    290                 295                 300

Val Thr Ser Glu Ser Gln Leu Phe Asn Lys Pro Tyr Trp Leu Gln Arg
305                 310                 315                 320

Ala Gln Gly His Asn Asn Gly Ile Cys Trp Gly Asn Gln Leu Phe Val
                325                 330                 335

Thr Val Val Asp Thr Thr Arg Ser Thr Asn Met Thr Leu Cys Ala Glu
            340                 345                 350
```

```
Val Lys Lys Glu Ser Thr Tyr Lys Asn Glu Asn Phe Lys Glu Tyr Leu
            355                 360                 365

Arg His Gly Glu Glu Phe Asp Leu Gln Phe Ile Phe Gln Leu Cys Lys
        370                 375                 380

Ile Thr Leu Thr Ala Asp Val Met Thr Tyr Ile His Lys Met Asp Ala
385                 390                 395                 400

Thr Ile Leu Glu Asp Trp Gln Phe Gly Leu Thr Pro Pro Pro Ser Ala
                405                 410                 415

Ser Leu Glu Asp Thr Tyr Arg Phe Val Thr Ser Thr Ala Ile Thr Cys
            420                 425                 430

Gln Lys Asn Thr Pro Pro Lys Gly Lys Glu Asp Pro Leu Lys Asp Tyr
        435                 440                 445

Met Phe Trp Glu Val Asp Leu Lys Glu Lys Phe Ser Ala Asp Leu Asp
    450                 455                 460

Gln Phe Pro Leu Gly Arg Lys Phe Leu Leu Gln Ala Gly Leu Gln Ala
465                 470                 475                 480

Arg Pro Lys Leu Lys Arg Pro Ala Ser Ser Ala Pro Arg Thr Ser Thr
                485                 490                 495

Lys Lys Lys Lys Val Lys Arg
            500
```

<210> SEQ ID NO 3
<211> LENGTH: 1512
<212> TYPE: DNA
<213> ORGANISM: Human Papillomavirus Type 52

<400> SEQUENCE: 3

```
atgtccgtgt ggcggcctag tgaggccact gtgtacctgc ctcctgtacc tgtctctaag     60
gttgtaagca ctgatgagta tgtgtctcgc acaagcatct attattatgc aggcagttct    120
cgattactaa cagtaggaca tcccttattt ctattaaaa acaccagtag tggtaatggt     180
aaaaaagttt tagttcccaa ggtgtctggc ctgcaataca gggtatttag aattaaattg    240
ccggacccta taaatttggg ttttccagat acatcttttt ataacccaga acccaaagg     300
ttggtgtggg cctgtacagg cttggaaatt ggtaggggac agcctttagg tgtgggtatt    360
agtgggcatc ctttattaaa caagtttgat gatactgaaa ccagtaacaa atatgctggt    420
aaacctggta tagataatag ggaatgttta tctatggatt ataagcagac tcagttatgc    480
attttaggat gcaaacctcc tataggtgaa cattggggta agggaacccc ttgtaataat    540
aattcaggaa atcctgggga ttgtcctccc ctacagctca ttaacagtgt aatacaggat    600
ggggacatgg tagatacagg atttggttgc atggatttta atccttgca agctagtaaa    660
agtgatgtgc ccattgatat atgtagcagt gtatgtaagt atccagatta tttgcaaatg    720
gctagcgagc catatggtga cagtttgttc tttttttctta gacgtgagca aatgtttgtt    780
agacactttt ttaatagggc cggtaccta ggtgaccctg tgccaggtga tttatatata     840
caagggtcta actctggcaa tactgccact gtacaaagca gtgcttttt tcctactcct    900
agtggttcta tggtaaccc agaatcccaa ttatttaata accgtactg gttacaacgt     960
gcgcagggcc acaataatgg catatgttgg ggcaatcagt gtttgtcac agttgtggat   1020
accactcgta gcactaacat gactttatgt gctgaggtta aaaaggaaag cacatataaa   1080
aatgaaaatt ttaaggaata ccttcgtcat ggcgaggaat ttgatttaca atttattttt   1140
caattgtgca aaattacatt aacagctgat gttatgacat acattcataa gatggatgcc   1200
```

```
actatttttag aggactggca atttggcctt accccaccac cgtctgcatc tttggaggac    1260
acatacagat ttgtcacttc tactgctata acttgtcaaa aaaacacgcc acctaaagga    1320
aaggaagatc ctttaaagga ctatatgttt tgggaggtgg atttaaaaga aaagtttct    1380 gcagatttag atcagtttcc tttaggtagg aagttttgt tacaggcagg gctacaggct    1440
aggcccaaac taaaacgccc tgcatcatcg gccccacgta cctccacaaa gaagaaaaag    1500
gttaaaaggt aa                                                        1512
```

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4

```
atgtccgtgt ggcggcctag t                                                21
```

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5

```
gagatctcaa ttacacaaag tg                                               22
```

<210> SEQ ID NO 6
<211> LENGTH: 31
<212> TYPE: DNA
<213> ORGANISM: Artificial Sequence
<220> FEATURE:
<223> OTHER INFORMATION: PCR Primer

<400> SEQUENCE: 6

```
gagatctcac aaaacaaaat gtccgtgtgg c                                     31
```

<210> SEQ ID NO 7
<211> LENGTH: 1512
<212> TYPE: DNA
<213> ORGANISM: Artificial Sequence
<220> FEATURE:
<223> OTHER INFORMATION: 52L1R antisense

<400> SEQUENCE: 7

```
tacaggcaga cctctggtag gcttcgatga cagatgaacg gtggtcaagg tcagagattc      60
caacagagat ggctgcttat gcagaggtct tggaggtaga tgatgatgcg accaaggaga    120
tctaacaact gacagccagt gggtatgaag agatagttct tgtggaggag gccattgcca    180
ttcttccaga accaaggttt ccagagacca acgttatgt ctcagaagtc ttagttcaac    240
ggtctgggtt tgttcaagcc aaagggtctg tgatcaaaga tgttgggtct ttgagtttct    300
aaccagaccc gaacatgacc aaacctttag ccatctccag ttggtaaccc acagccatag    360
agaccagtgg gtaacaactt gttcaagctg ctgtgacttt ggagattgtt catgcgacca    420
ttcggtccat agctattgtc tcttacaaac agatacctga tgttcgtttg agttaacaca    480
tagaacccaa cattcggtgg ttagccactt gtgaccccat tcccatgagg tacattgttg    540
ttgagaccat tgggtccact gacaggtggt aacgttaact agttgaggca gtaggttctg    600
ccactgtacc agctgtgacc aaagccaaca tacctgaagt tgtggaacgt tcgaagattc    660
```

```
aggctgcagg gttagctgta gacaaggaga cagacattca tgggtctgat gaacgtttac      720
cgaagacttg gtatgccact gaggaacaag aagaagaact cttctcttgt ttacaagcag      780
tctgtgaaga agttgtctcg accatggaac ccactgggtc aaggtccact gaacatgtag      840
gttccaaggt tgagaccatt gtgacgatga caggttagga gacgaaagaa gggttgaggt      900
agaccaaggt accagtggag gcttagggtt aacaagttgt tcggtatgac caacgtttct      960
cgagttccag tgttgttgcc atagacaacc ccattggtta acaagcagtg gcagcagctg     1020
tgatgatcta gatgattgta ctggaacaca cgacttcagt tcttccttag gtggatgttc     1080
ttgcttttga agttccttat gaactctgtg ccacttctta agctgaacgt taagtagaag     1140
gttaacacat tctagtggaa ctggcgactg cagtactgaa tgtaggtgtt ctacctgcga     1200
tgatagaacc ttctgaccgt taagccaaac tgaggtggtg gtaggcgaag gaaccttctg     1260
tgaatgtcta agcagtgaag gtgacgatag tggacagttt tcttgtgagg tggtttccca     1320
ttccttctgg gtaacttcct gatgtacaag acccttcagc tgaacttcct tttcaagaga     1380
cgactgaacc tggttaaggg taacccatct ttcaagaaca acgttcgacc aaacgttcga     1440
tctggtttca acttctctgg tcgatcgaga cgaggttctt gaaggtggtt cttcttcttc     1500
cagttctcta tt                                                         1512
```

OPTIMIZED EXPRESSION OF HPV 52 L1 IN YEAST

CROSS-REFERENCE TO RELATED APPLICATIONS

This application is a 371 National Stage Application of PCT/US2005/009199, international filing date of Mar. 18, 2005, which claims the benefit of U.S. Provisional Application No. 60/555,926, filed Mar. 24, 2004, now expired.

FIELD OF THE INVENTION

The present invention relates generally to the prevention and/or therapy of human papillomavirus (HPV) infection. More specifically, the present invention relates to synthetic polynucleotides encoding HPV 52 L1 protein, and to recombinant vectors and hosts comprising said polynucleotides. This invention also relates to HPV 52 virus-like particles (VLPs), wherein the VLPs are produced by expressing recombinant HPV 52 L1 or L1+L2 in yeast cells and to their use in vaccines and pharmaceutical compositions for preventing and treating HPV infections.

BACKGROUND OF THE INVENTION

There are more than 80 types of human papillomavirus (HPV), many of which have been associated with a wide variety of biological phenotypes, from benign proliferative warts to malignant carcinomas (for review, see McMurray et al., *Int. J. Exp. Pathol.* 82(1): 15-33 (2001)). HPV6 and HPV11 are the types most commonly associated with benign warts, nonmalignant condyloma acuminata and/or low-grade dysplasia of the genital or respiratory mucosa. HPV16 and HPV18 are the high-risk types most frequently associated with in situ and invasive carcinomas of the cervix, vagina, vulva and anal canal. More than 90% of cervical carcinomas are associated with infections of HPV16, HPV18 or the less prevalent oncogenic types HPV31, -33, -45, -52 and -58 (Schiffman et al., *J. Natl. Cancer Inst.* 85(12): 958-64 (1993)). The observation that HPV DNA is detected in 90-100% of cervical cancers provides strong epidemiological evidence that HPVs cause cervical carcinoma (see Bosch et al., *J. Clin. Pathol.* 55: 244-265 (2002)).

Papillomaviruses are small (50-60 nm), nonenveloped, icosahedral DNA viruses that encode up to eight early and two late genes. The open reading frames (ORFs) of the viral genomes are designated E1 to E7, and L1 and L2, where "E" denotes early and "L" denotes late. L1 and L2 code for virus capsid proteins, while the E genes are associated with functions such as viral replication and cellular transformation.

The L1 protein is the major capsid protein and has a molecular weight of 55-60 kDa. The L2 protein is the minor capsid protein. Immunological data suggest that most of the L2 protein is internal to the L1 protein in the viral capsid. Both the L1 and L2 proteins are highly conserved among different papillomaviruses.

Expression of the L1 protein or a combination of the L1 and L2 proteins in yeast, insect cells, mammalian cells or bacteria leads to self-assembly of virus-like particles (VLPs) (for review, see Schiller and Roden, in *Papillomavirus Reviews: Current Research on Papillomaviruses*; Lacey, ed. Leeds, UK: Leeds Medical Information, pp 101-12 (1996)). VLPs are morphologically similar to authentic virions and are capable of inducing high titres of neutralizing antibodies upon administration into animals or humans. Because VLPs do not contain the potentially oncogenic viral genome, they present a safe alternative to the use of live virus in HPV vaccine development (for review, see Schiller and Hidesheim, *J. Clin. Virol.* 19: 67-74 (2000)). For this reason, the L1 and L2 genes have been identified as immunological targets for the development of prophylactic and therapeutic vaccines for HPV infection and disease.

HPV vaccine development and commercialization have been hindered by difficulties associated with obtaining high expression levels of capsid proteins in successfully transformed host organisms, limiting the production of purified protein. Therefore, despite the identification of wild-type nucleotide sequences encoding HPV L1 proteins such as HPV 52 L1 protein, it would be highly desirable to develop a readily renewable source of crude HPV L1 protein that utilizes HPV 52 L1-encoding nucleotide sequences that are optimized for expression in the intended host cell. Additionally, it would be useful to produce large quantities of HPV 52 L1 VLPs having the immunity-conferring properties of the native proteins for use in vaccine development.

SUMMARY OF THE INVENTION

The present invention relates to compositions and methods to elicit or enhance immunity to the protein products expressed by HPV 52 L1 genes. Specifically, the present invention provides polynucleotides encoding HPV 52 L1 protein, wherein the polynucleotides have been codon-optimized for high level expression in a yeast cell. In alternative embodiments of the invention, the nucleotide sequence of the polynucleotide is altered to eliminate transcription termination signals that are recognized by yeast. The present invention further provides HPV 52 virus-like particles (VLPs), wherein said VLPs are produced by expressing recombinant HPV 52 L1 or L1+L2 in yeast cells, and discloses use of HPV 52 VLPs in immunogenic compositions and vaccines for the prevention and/or treatment of HPV disease and HPV-associated cancer.

The present invention relates to synthetic DNA molecules encoding the HPV 52 L1 protein. The codons of the synthetic molecules are designed so as to use the codons preferred by a yeast cell. In an alternative embodiment of the invention, the nucleotide sequence of the synthetic molecule is altered to eliminate transcription termination signals that are recognized by yeast. The synthetic molecules may be used as a source of HPV 52 L1 protein, which may self-assemble into VLPs. Said VLPs may be used in a VLP-based vaccine.

An exemplary embodiment of the present invention comprises a synthetic nucleic acid molecule which encodes the HPV 52 L1 protein as set forth in SEQ ID NO:2, said nucleic acid molecule comprising a sequence of nucleotides that is codon-optimized for high-level expression in a yeast cell.

Also provided are recombinant vectors and recombinant host cells, both prokaryotic and eukaryotic, which contain the nucleic acid molecules disclosed throughout this specification. In a preferred embodiment of the present invention, the host cell is a yeast cell.

The present invention also relates to a process for expressing an HPV 52 L1 protein in a recombinant host cell, comprising: (a) introducing a vector comprising a nucleic acid encoding an HPV 52 L1 protein into a yeast host cell; and (b) culturing the yeast host cell under conditions which allow expression of said HPV 52 L1 protein.

The present invention further relates to a process for expressing an HPV 52 L1 protein in a recombinant host cell, comprising: (a) introducing a vector comprising a nucleic acid molecule encoding an HPV 52 L1 protein into a yeast host cell; wherein the nucleic acid molecule is codon-optimized for optimal expression in the yeast host cell and; (b) culturing the yeast host cell under conditions which allow expression of said HPV 52 L1 protein.

In preferred embodiments, the nucleic acid molecule comprises a sequence of nucleotides as set forth in SEQ ID NO:1 (designated herein "52 L1 R sequence").

This invention also relates to HPV 52 virus-like particles (VLPs) which are produced in yeast cells, methods of producing HPV 52 VLPs, and methods of using HPV 52 VLPs.

In a preferred embodiment of the invention, the yeast is selected from the group consisting of: *Saccharomyces cerevisiae, Hansenula polymorpha, Pichia pastoris, Kluyvermyces fragilis, Kluveromyces lactis,* and *Schizosaccharomyces pombe.*

Another aspect of this invention is an HPV 52 VLP, wherein the VLP is produced by recombinant expression of HPV 52 L1 or HPV 52 L1+L2 in a yeast cell.

Yet another aspect of this invention is an HPV 52 VLP which comprises an HPV 52 L1 protein produced by a codon-optimized HPV 52 L1 gene. In an exemplary embodiment of this aspect of the invention, the codon-optimized HPV 52 L1 gene comprises a sequence of nucleotides as set forth in SEQ ID NO:1.

This invention also provides a method for inducing an immune response in an animal comprising administering HPV 52 virus-like particles to the animal. In a preferred embodiment, the HPV 52 VLPs are produced by a codon-optimized gene.

Yet another aspect of this invention is a method of preventing or treating HPV-associated cervical cancer comprising administering to a mammal a vaccine comprising HPV 52 VLPs. In a preferred embodiment of this aspect of the invention, the HPV 52 VLPs are produced in yeast.

This invention also relates to a vaccine comprising HPV 52 virus-like particles (VLPs), wherein the HPV 52 VLPs are produced in yeast.

In an alternative embodiment of this aspect of the invention, the vaccine further comprises VLPs of at least one additional HPV type. The at least one additional HPV type may be any HPV type of interest, including any HPV type described in the art or those subsequently identified. In a preferred embodiment, the HPV type is a type that is associated with a clinical phenotype such as warts or cervical cancer. In a further preferred embodiment, the at least one additional HPV type is selected from the group consisting of: HPV6, HPV11, HPV16, HPV18, HPV31, HPV33, HPV35, HPV39, HPV45, HPV51, HPV55, HPV56, HPV58, HPV59, and HPV68.

This invention also relates to pharmaceutical compositions comprising HPV 52 virus-like particles, wherein the HPV 52 VLPs are produced in yeast. Further, this invention relates to pharmaceutical compositions comprising HPV 52 VLPs and VLPs of at least one additional HPV type. In a preferred embodiment, the at least one additional HPV type is selected from the group consisting of: HPV6, HPV11, HPV16, HPV18, HPV31, HPV33, HPV35, HPV39, HPV45, HPV51, HPV55, HPV56, HPV58, HPV59, and HPV68.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or "upstream activating sequences" or inhibiting sequences termed "silencers".

The term "vector" refers to some means by which DNA fragments can be introduced into a host organism or host tissue. There are various types of vectors including plasmids, viruses (including adenovirus), bacteriophages and cosmids.

The term "cassette" refers to a nucleotide or gene sequence that is to be expressed from a vector, for example, the nucleotide or gene sequence encoding the HPV 52 L1 protein. In general, a cassette comprises a gene sequence inserted into a vector which, in some embodiments, provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences.

The designations "52 L1 wild-type sequence" and "52 L1 wt sequence" refer to the HPV 52 L1 sequence disclosed herein as SEQ ID NO:3. Although the HPV 52 L1 wild-type sequence has been described previously, it is not uncommon to find minor sequence variations between DNAs obtained from clinical isolates. Therefore, a representative HPV 52 L1 wild-type sequence was isolated from clinical samples previously shown to contain HPV 52 DNA (see EXAMPLE 1). The HPV 52 L1 wild-type sequence was used as a reference sequence to compare the codon-optimized HPV 52 L1 sequences disclosed herein (see FIG. 1).

The designations "HPV 52 L1 R" and "52 L1 R" refer to an exemplary synthetic HPV52 L1 nucleotide sequence (SEQ ID NO:1), disclosed herein, wherein the sequence was rebuilt so that it comprises codons that are preferred for high-level expression by a yeast cell.

The term "effective amount" means sufficient vaccine composition is introduced to produce the adequate levels of the polypeptide, so that an immune response results. One skilled in the art recognizes that this level may vary.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "mammalian" refers to any mammal, including a human being.

"VLP" or "VLPs" mean(s) virus-like particle or virus-like particles.

"Synthetic" means that the HPV 52 L1 gene was created so that it contains a sequence of nucleotides that is not the same as the sequence of nucleotides present in the designated naturally occurring wild-type HPV 52 L1 gene (52 L1 wt, SEQ ID NO:3). As stated above, synthetic molecules are provided herein comprising a sequence of nucleotides comprising codons that are preferred for expression by yeast cells. The synthetic molecules provided herein encode the same amino acid sequences as the wild-type HPV 52 L1 gene (SEQ ID NO:2).

BRIEF DESCRIPTION OF THE DRAWINGS

FIG. 1 shows a sequence alignment comparing nucleotides that were altered in the synthetic HPV 52 L1 gene of the present invention (SEQ ID NO:1, indicated as "52 L1 R") (See EXAMPLE 2). The reference sequence is the 52 L1 wild-type sequence (SEQ ID NO:3, indicated as "52 L1 wt"; see EXAMPLE 1). Altered nucleotides are indicated at their corresponding location. Nucleotide number is contained within the parentheses. Identical nucleotides in the 52 L1 rebuilt sequence are indicated with dots.

FIG. 2 shows the rebuilt synthetic HPV 52 L1 double-stranded nucleic acid (SEQ ID NOs:1 and 7) and single-code amino acid sequence (SEQ ID NO:2). Nucleotide number is indicated to the left.

DETAILED DESCRIPTION OF THE INVENTION

Figure 3:
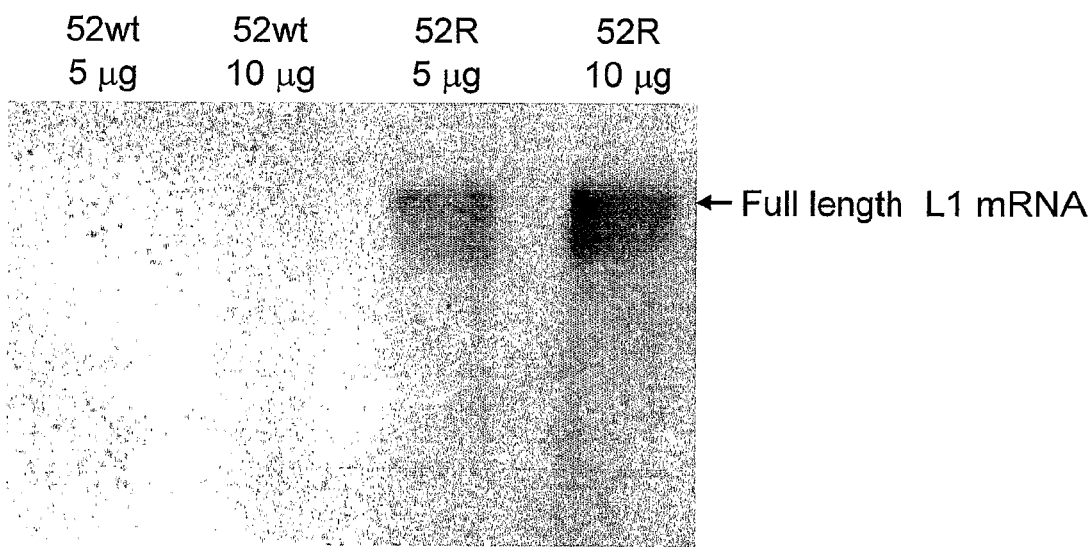
FIG. 3 shows a Northern blot of HPV 52 L1 wt and HPV 52 L1 R transcripts (see EXAMPLE 4). The blot was probed with a mixture of DNA probes generated against both the 52 L1 wt and the 52 L1 R sequences. The arrow on right indicates the predicted position of a full-length 52 L1 transcript. No transcripts of any length were detected in the 5 and 10 µg lanes of 52 L1 wt RNA. Full-length transcripts are apparent in the 52 L1 R, in both the 5 and 10 µg lanes.

The majority of cervical carcinomas are associated with infections of specific oncogenic types of human papillomavirus (HPV). The present invention relates to compositions and methods to elicit or enhance immunity to the protein products expressed by genes of oncogenic HPV types. Specifically, the present invention provides polynucleotides encoding HPV 52 L1, wherein the polynucleotides are codon-optimized for high-level expression in yeast. The present invention also provides HPV52 virus-like particles (VLPs), which are produced in yeast, and discloses use of said polynucleotides and VLPs in immunogenic compositions and vaccines for the prevention and/or treatment of HPV-associated cancer.

A wild-type HPV52 L1 nucleotide sequence has been reported (Genbank Accession # NC 001592). The present invention provides synthetic DNA molecules encoding the HPV 52 L1 protein. In one aspect of the invention, the synthetic molecules comprise a sequence of codons, wherein at least some of the codons have been altered to use the codons preferred by a yeast cell for high-level expression. In an alternative aspect of the invention, the nucleotide sequence of the synthetic molecule is altered to eliminate transcription termination signals that are recognized by yeast. The synthetic molecules may be used as a coding sequence for expression of HPV 52 L1 protein, which may self-assemble into VLPs. Said VLPs may be used in a VLP-based vaccine to provide effective immunoprophylaxis against papillomavirus infection through neutralizing antibody and cell-mediated immunity. Such VLP-based vaccines may also be useful for treatment of already established HPV infections.

Expression of HPV VLPs in yeast cells offers the advantages of being cost-effective and easily adapted to large-scale growth in fermenters. In addition, the yeast genome can be readily altered to ensure selection of recombinant, transformed yeast with increased growth and expression potential. However, many HPV L1 proteins, including HPV 52 L1 are expressed at levels in yeast cells which are lower than what is desirable for commercial scale-up (see EXAMPLE 2).

Accordingly, the present invention relates to HPV 52 L1 gene sequences that are "optimized" for high-level expression in a yeast cellular environment.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon use frequencies for microorganisms has revealed endogenous DNA of E. coli most commonly contains the CTG leucine-specifying codon, while the DNA of yeasts and slime molds most commonly includes a TTA leucine-specifying codon. In view of this hierarchy, it is generally believed that the likelihood of obtaining high levels of expression of a leucine-rich polypeptide by an E. coli host will depend to some extent on the frequency of codon use. For example, it is likely that a gene rich in TTA codons will be poorly expressed in E. coli, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant protein expression. Thus, one aspect of this invention is an HPV 52 L1 gene that is codon-optimized for high-level expression in a yeast cell. In a preferred embodiment of this invention, it has been found that the use of alternative codons encoding the same protein sequence may remove the constraints on expression of HPV 52 L1 proteins by yeast cells.

In accordance with this invention, HPV 52 L1 gene segments were converted to sequences having identical translated sequences but with alternative codon usage as described by Sharp and Cowe (Synonymous Codon Usage in *Saccharomyces cerevisiae. Yeast* 7: 657-678 (1991)), which is hereby incorporated by reference. The methodology generally consists of identifying codons in the wild-type sequence that are not commonly associated with highly expressed yeast genes and replacing them with optimal codons for high expression in yeast cells. The new gene sequence is then inspected for undesired sequences generated by these codon replacements (e.g., "ATTTA" sequences, inadvertent creation of intron splice recognition sites, unwanted restriction enzyme sites, high GC content, presence of transcription termination signals that are recognized by yeast, etc.). Undesirable sequences are eliminated by substitution of the existing codons with different codons coding for the same amino acid. The synthetic gene segments are then tested for improved expression.

The methods described above were used to create synthetic gene segments for HPV 52 L1, resulting in a gene comprising codons optimized for high-level expression. While the above procedure provides a summary of our methodology for designing codon-optimized genes for use in HPV vaccines, it is understood by one skilled in the art that similar vaccine efficacy or increased expression of genes may be achieved by minor variations in the procedure or by minor variations in the sequence.

Accordingly, the present invention relates to a synthetic polynucleotide comprising a sequence of nucleotides encoding an HPV 52 L1 protein, or a biologically active fragment or mutant form of an HPV 52 L1 protein, the polynucleotide sequence comprising codons optimized for expression in a yeast host cell. Said mutant forms of the HPV 52 L1 protein include, but are not limited to: conservative amino acid substitutions, amino-terminal truncations, carboxy-terminal truncations, deletions, or additions. Any such biologically active fragment and/or mutant will encode either a protein or protein fragment which at least substantially mimics the immunological properties of the HPV 52 L1 protein as set forth in SEQ ID NO:2. The synthetic polynucleotides of the present invention encode mRNA molecules that express a functional HPV 52 L1 protein so as to be useful in the development of a therapeutic or prophylactic HPV vaccine.

One aspect of this invention is a codon-optimized nucleic acid molecule which encodes the HPV 52 L1 protein as set forth in SEQ ID NO:2, said nucleic acid molecule comprising a sequence of nucleotides that are codon-optimized for high-level expression in a yeast cell. In a preferred embodiment of this aspect of the invention, the nucleic acid molecule comprises a sequence of nucleotides as set forth in SEQ ID NO:1.

The present invention also relates to recombinant vectors and recombinant host cells, both prokaryotic and eukaryotic, which contain the nucleic acid molecules disclosed throughout this specification. In a preferred embodiment of this invention, the host cell is a yeast host cell.

The synthetic HPV 52 L1 DNA, functional equivalents thereof, and fragments thereof, constructed through the methods described herein may be recombinantly expressed by molecular cloning into an expression vector containing a suitable promoter and other appropriate transcription regulatory elements. Said expression vector may be transferred into prokaryotic or eukaryotic host cells to produce recombinant HPV 52 L1 protein. Techniques for such manipulations are fully described in the art (Sambrook et al. *Molecular Cloning: A Laboratory Manual*; Cold Spring Harbor Laboratory, Cold Spring Harbor, N.Y., (1989); *Current Protocols in Molecular Biology*, Ausubel et al., Green Pub. Associates and Wiley-Interscience, New York (1988); *Yeast Genetics: A Laboratory Course Manual*, Rose et al., Cold Spring Harbor Laboratory, Cold Spring Harbor, N.Y., (1990), which are hereby incorporated by reference in their entirety).

Thus, the present invention relates to a process for expressing an HPV 52 L1 protein in a recombinant host cell, comprising: (a) introducing a vector comprising a nucleic acid encoding an HPV 52 L1 protein into a yeast host cell; and (b) culturing the yeast host cell under conditions which allow expression of said HPV 52 L1 protein.

The present invention further relates to a process for expressing an HPV 52 L1 protein in a recombinant host cell, comprising: (a) introducing a vector comprising a nucleic acid encoding an HPV 52 L1 protein into a yeast host cell; wherein the nucleic acid molecule is codon-optimized for optimal expression in the yeast host cell and; (b) culturing the yeast host cell under conditions which allow expression of said HPV 52 L1 protein.

This invention further relates to a process for expressing an HPV 52 L1 protein in a recombinant host cell, comprising: (a) introducing a vector comprising a nucleic acid as set forth in SEQ ID NO:1 into a yeast host cell; and, (b) culturing the yeast host cell under conditions which allow expression of said HPV 52 L1 protein.

The synthetic genes of the present invention can be assembled into an expression cassette that comprises sequences designed to provide efficient expression of the HPV 52 L1 protein in the host cell. The cassette preferably contains the synthetic gene, with related transcriptional and translational control sequences operatively linked to it, such as a promoter, and termination sequences. In a preferred embodiment, the promoter is the *S. cerevisiae* GAL1 promoter, although those skilled in the art will recognize that any of a number of other known yeast promoters such as the GAL10, GAL7, ADH1, TDH3 or PGK promoters, or other eukaryotic gene promoters may be used. A preferred transcriptional terminator is the *S. cerevisiae* ADH1 terminator, although other known transcriptional terminators may also be used. The combination of GAL1 promoter-ADH1 terminator is particularly preferred.

Another aspect of this invention is an HPV 52 virus-like particle (VLP) produced by recombinantly expressing the HPV 52 L1 or L1+L2 genes in a yeast cell, methods of producing HPV 52 VLPs, and methods of using HPV 52 VLPs. VLPs can self-assemble when L1, the major capsid protein of human and animal papillomaviruses, is expressed in yeast, insect cells, mammalian cells or bacteria (for review, see Schiller and Roden, in *Papillomavirus Reviews: Current Research on Papillomaviruses*; Lacey, ed. Leeds, UK: Leeds Medical Information, pp 101-12 (1996)). Morphologically indistinct HPV VLPs can also be produced by expressing a combination of the L1 and L2 capsid proteins. VLPs are composed of 72 pentamers of L1 in a T=7 icosahedral structure (Baker et al., *Biophys. J.* 60(6): 1445-56 (1991)).

VLPs are morphologically similar to authentic virions and are capable of inducing high titres of neutralizing antibodies upon administration into an animal. Immunization of rabbits (Breitburd et al., *J. Virol.* 69(6): 3959-63 (1995)) and dogs (Suzich et al., *Proc. Natl. Acad. Sci. USA* 92(25): 11553-57 (1995)) with VLPs was shown to both induce neutralizing antibodies and protect against experimental papillomavirus infection. Additionally, immunization of adult women with HPV 16 VLPs was shown to protect against HPV 16 infection and HPV 16 cervical intraepithelial neoplasia (Koutsky et al. *N. Engl. J. Med.* 347: 1645-51 (2002)). Because VLPs do not contain the potentially oncogenic viral genome and can self-assemble when expressed from a single gene, they present a safe alternative to the use of live virus in HPV vaccine development (for review, see Schiller and Hidesheim, *J. Clin. Virol.* 19: 67-74 (2000)).

Thus, the present invention relates to virus-like particles comprised of recombinant L1 protein or recombinant L1+L2 proteins of HPV 52, wherein the recombinant protein is expressed in a yeast cell.

As stated above, in a preferred embodiment of the invention, the HPV 52 VLPs are produced in yeast. In a further preferred embodiment, the yeast is selected from the group consisting of: *Saccharomyces cerevisiae, Hansenula polymorpha, Pichia pastoris, Kluyveromyces fragilis, Kluyveromyces lactis*, and *Schizosaccharomyces pombe*.

Another aspect of this invention is an HPV 52 VLP which comprises an HPV 52 L1 protein produced by a codon-optimized HPV 52 L1 gene. In a preferred embodiment of this aspect of the invention, the codon-optimized HPV 52 L1 gene comprises a sequence of nucleotides as set forth in SEQ ID NO:1.

Yet another aspect of this invention is a method of producing HPV 52 VLPs, comprising: (a) transforming yeast with a recombinant DNA molecule encoding HPV 52 L1 protein or HPV 52 L1+L2 proteins; (b) cultivating the transformed yeast under conditions that permit expression of the recombinant DNA molecule to produce the recombinant HPV 52 protein; and (c) isolating the recombinant HPV 52 protein to produce HPV52 VLPs.

In a preferred embodiment of this aspect of the invention, the yeast is transformed with a codon-optimized HPV 52 L1 gene to produce HPV 52 VLPs. In a particularly preferred embodiment, the codon-optimized HPV 52 L1 gene comprises a sequence of nucleotides as set forth in SEQ ID NO:1.

This invention also provides a method for inducing an immune response in an animal comprising administering HPV 52 virus-like particles to the animal. In a preferred embodiment, the HPV 52 VLPs are produced by recombinantly expressing a codon-optimized gene encoding HPV 52 L1 or HPV 52 L1+L2.

Yet another aspect of this invention is a method of preventing and/or treating HPV-associated cervical cancer comprising administering to a mammal a vaccine comprising HPV 52 VLPs. In a preferred embodiment of this aspect of the invention, the HPV 52 VLPs are produced in yeast.

This invention also relates to a vaccine comprising HPV 52 virus-like particles (VLPs).

In an alternative embodiment of this aspect of the invention, the vaccine further comprises VLPs of at least one additional HPV type. In a preferred embodiment, the at least one additional HPV type is selected from the group consisting of: HPV 6, HPV 11, HPV 16, HPV 18, HPV 31, HPV 33, HPV 35, HPV 39, HPV 45, HPV 51, HPV 55, HPV 56, HPV 58, HPV 59, and HPV 68.

In a preferred embodiment of this aspect of the invention, the vaccine further comprises HPV 16 VLPs.

In another preferred embodiment of the invention, the vaccine further comprises HPV 16 VLPs and HPV 18 VLPs.

In yet another preferred embodiment of the invention, the vaccine further comprises HPV 6 VLPs, HPV 11 VLPs, HPV 16 VLPs and HPV 18 VLPs.

This invention also relates to pharmaceutical compositions comprising HPV 52 virus-like particles. Further, this invention relates to pharmaceutical compositions comprising HPV 52 VLPs and VLPs of at least one additional HPV type. In a preferred embodiment, the at least one additional HPV type is selected from the group consisting of: HPV 6, HPV 11, HPV 16, HPV 18, HPV 31, HPV 33, HPV 35, HPV 39, HPV 45, HPV 51, HPV 55, HPV 56, HPV 58, HPV 59, and HPV 68.

Vaccine compositions of the present invention may be used alone at appropriate dosages which allow for optimal inhibition of HPV 52 infection with minimal potential toxicity. In addition, co-administration or sequential administration of other agents may be desirable.

The amount of virus-like particles to be introduced into a vaccine recipient will depend on the immunogenicity of the expressed gene product. In general, an immunologically or prophylactically effective dose of about 10 µg to 100 µg, and preferably about 20 µg to 60 µg of VLPs is administered directly into muscle tissue. Subcutaneous injection, intradermal introduction, impression though the skin, and other modes of administration such as intraperitoneal, intravenous, or inhalation delivery are also contemplated. It is also contemplated that booster vaccinations may be provided. Parenteral administration, such as intravenous, intramuscular, subcutaneous or other means of administration with adjuvants such as alum or Merck alum adjuvant, concurrently with or subsequent to parenteral introduction of the vaccine of this invention is also advantageous.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Determination of a Representative HPV 52 L1 Sequence

The HPV 52 L1 sequence has been described previously (Genbank Accession # NC 001592). It is not uncommon, however, to find minor sequence variations between DNAs obtained from clinical isolates. To determine a representative HPV 52 L1 wild-type sequence, DNA was isolated from three clinical samples previously shown to contain HPV 52 DNA. HPV 52 L1 sequences were amplified in a polymerase chain reaction (PCR) using Taq DNA polymerase and the following primers: 5' L1 5'-A T G T C C G T G T G G C G G C C T A G T-3' (SEQ ID NO:4) and 3' 52 Bgl II 5'-G A G A T C T C A A T T A C A C A A A G T G-3' (SEQ ID NO:5). The amplified products were electrophoresed on agarose gels and visualized by ethidium bromide staining. The ~1500 bp L1 bands were excised and DNA was purified using Geneclean Spin Kit (Q-Bio Gene, Carlsbad, Calif.). The DNA was then ligated to the TA cloning vector, pCR2.1 (Invitrogen). TOP10F' *E. coli* cells were transformed with the ligation mixture and plated on LB agar with kanamycin plus IPTG and X-gal for blue/white colony selection. The plates were inverted and incubated for 16 hours at 37° C.

Colony PCR was performed on five white colonies originating from each of the three clinical isolates amplified. 5' L1 and 3' 52 Bgl II primers were used in a two-step PCR in which the first step comprised 10 cycles of 96° C. for 15 seconds (denaturing), 55° C. for 30 seconds (annealing) and 68° C. for 2 minutes (extension), and the second step comprised 35 cycles of an essentially similar program, except the annealing step was performed at 50° C. for 30 seconds. PCR products were electrophoresed on agarose gels and visualized by ethidium bromide staining. Several colonies from each clinical isolate contained amplified products with ~1500 bp bands. The colonies were cultured in LB medium with kanamycin, shaking at 37° C. for 16 hours. Minipreps were performed to extract the plasmid DNAs, which were digested with restriction endonucleases to demonstrate the presence of the L1 gene in the plasmid. The resulting restriction fragments were viewed by agarose gel electrophoresis and ethidium bromide staining.

DNA sequencing was performed on plasmids containing cloned L1 inserts from each of the three clinical isolates. DNA and translated amino acid sequences were compared with one another and the previously published Genbank HPV 52 L1 sequences. Sequence analysis of the three clinical isolates revealed that no sequence was identical to the Genbank sequence (Accession No. NC 001592). The pCR2.1 HPV 52 L1 clone #2C was chosen to be the representative HPV 52 L1 sequence and is referred to herein as the "52 L1 wild-type sequence" (SEQ ID NO:3, see FIG. 1). The sequence chosen as 52 L1 wild-type (wt) contained one point mutation when compared to the Genbank sequence, which consisted of a silent mutation at nucleotide 1308 (adenine→guanine). The amino acid sequence of the HPV 52 L1 wt sequence was identical to the 52 L1 Genbank sequence.

The HPV 52 L1 wild-type sequence was amplified using the 5' L1 Bgl II primer (5'-G A G A T C T C A C A A A A C A A A A T G T C C G T G T G G C-3' (SEQ ID NO:6)) and the 3' 52 Bgl II primer described above to add Bgl II extensions. PCR was performed using Taq polymerase. The PCR product was electrophoresed on an agarose gel and visualized by ethidium bromide staining. The ~1500 bp band was excised and DNA was purified using the Geneclean Spin kit (Q-Bio Gene, Carlsbad, Calif.). The PCR product was then ligated to the pCR2.1 vector and TOP10F' cells were transformed with the ligation mixture. White colonies were cultured in LB medium with kanamycin, shaking at 37° C. for 16 hours. Minipreps were performed to extract the plasmid DNA. The HPV 52 L1 gene was released from the vector sequences with Bgl II restriction endonuclease digestions. The digested DNA was subjected to agarose gel electrophoresis and viewed by ethidium bromide staining. The L1 band was purified using the Geneclean kit and ligated to a dephosphorylated, BamHI-digested pGAL110 vector. TOP10F' *E. coli* cells were transformed with the ligation mixture. To screen for the HPV 52 L1 insert in the correct orientation, plasmid DNA from the colonies was PCR-amplified. DNA sequencing was conducted to confirm the sequence and orientation of the inserts. The selected clone was named pGAL110-HPV 52 µl #5. Maxiprep DNA from the selected clone was prepared. *Saccharomyces cerevisiae* cells were made competent by spheroplasting with glusulase and transformed with pGAL110-HPV 52L1 #5. The yeast transformation mixture was plated in Leu⁻ sorbitol top-agar on Leu⁻ sorbitol plates and incubated inverted for 3-5 days at 30° C. Colonies were picked and streaked for isolation on Leu⁻ sorbitol plates. Isolated colonies were subsequently grown in 5 ml of 5×Leu⁻ Ade⁻ sorbitol with 1.6% glucose and 4% galactose in rotating tube cultures at 30° C. to induce HPV 52 L1 transcription and protein expression.

EXAMPLE 2

Yeast Codon Optimization

Yeast-preferred codons have been described (Sharp, Paul M and Cowe, Elizabeth. Synonymous Codon Usage in *Saccharomyces cerevisiae* YEAST 7: 657-678 (1991)). Expression of the HPV 52 L1 wt protein was detectable; however, the level of transcription was very low and not detectable by Northern blot. It was postulated that pre-mature transcription termination may be responsible for the low expression levels of the HPV 52 L1 gene. To increase transcription of this gene and ensure full-length transcripts would be produced, the HPV 52 L1 gene was rebuilt utilizing yeast-preferred codons. The sequence was inspected for the presence of yeast transcription termination signals that are recognized by yeast, and these sequences were eliminated by substitution with alternative codons, while preserving the same amino acid sequence. The rebuilt HPV 52 L1 sequence, which comprises yeast codon-optimized sequences, contained 379 nucleotide alterations compared to the HPV 52 L1 wt sequence. The resulting sequence is referred to herein as "52 L1 R" (R=rebuild, see FIG. 1). The nucleotide alterations between the 52 L1 wt (SEQ ID NO:3) and 52 L1 R (SEQ ID NO:1) sequences are shown in FIG. 1. The translated amino acid sequence of 52 L1 R was not altered (SEQ ID NO:2, see FIG. 2). The rebuilt sequence provides increased HPV 52 L1 protein expression, which is a significant advance over the wild-type for use in vaccine development.

The strategy employed to produce the optimized gene was to design long overlapping sense and antisense oligomers that span the gene, substituting nucleotides with yeast-preferred codon sequences while maintaining the amino acid sequence. These oligomers were used in place of template DNA in a PCR reaction with Pfu DNA polymerase. Additional amplification primers were designed and used to amplify the rebuilt sequences from template oligomers.

The optimal conditions for amplification were section-specific; however, most reactions employed a program resembling 94° C. for 5 minutes (denaturing) followed by 25 cycles of 95° C. for 30 sec (denaturing), 50-55° C. for 30 sec (annealing), 72° C. for 1.5 minute (extension), followed by a 72° C. for 7 minute final extension and 4° C. hold. PCR products were examined by agarose gel electrophoresis. Bands of the appropriate size were excised and the DNA was purified from the gel slice. The amplified fragments were then used as templates to assemble the 1512 nt rebuilt HPV 52 L1 gene.

Following rebuild, the 1512 nt band was gel purified, and ligated to pCR4 Blunt vector (Invitrogen, Carlsbad, Calif.). Following ligation, competent *E. coli* TOP10 cells were transformed with the ligation mixture. Colonies were grown in 4 ml LB with ampicillin and plasmid DNA was extracted from the colonies by miniprep techniques. The plasmid DNA was sequenced to confirm the presence of the desired HPV 52 L1 rebuild changes. To add BamHI extensions to both ends, the 52 L1 R (rebuild) was re-amplified from pCR4Blunt-52 L1 R. The amplified fragment was cloned as above and the resulting plasmid DNA was sequenced. The plasmid, pCR4 Blunt-52 L1 R (Bam) was digested with BamHI and the resulting DNA fragment inserts were electrophoresed on an agarose gel. The ~1530 bp HPV 52 L1 R (Bam) fragment was gel purified and ligated to BamHI-digested pGAL110. TOP10F' *E. coli* (Invitrogen) cells were transformed with the ligation mixture.

The resulting colonies were screened by PCR for the HPV 52 L1 R insert in the correct orientation. Sequence and orientation were confirmed by DNA sequencing. Maxiprep plasmid DNA was prepared. *S. cerevisiae* cells were made competent by spheroplasting and transformed. The yeast transformation was plated in Leu⁻ sorbitol top-agar on Leu⁻ sorbitol agar plates and incubated inverted for 7 days. Colonies were picked and streaked for clonal isolation on Leu⁻ sorbitol agar plates. Isolated colonies were subsequently grown in 5 ml of 5×Leu⁻ Ade⁻ sorbitol with 1.6% glucose and 4% galactose in rotating tube cultures at 30° C. to induce L1 transcription and protein expression. After 48 and/or 72 hours, a culture volume equivalent to an $OD_{600}$=10 was pelleted, the supernatant was removed and the pellets were frozen and stored −70° C.

EXAMPLE 3

RNA Preparation

Cell pellets of transformed yeast induced to express HPV 52 L1 by galactose induction were thawed on ice, suspended in 0.8 ml of Trizol reagent (Life Technologies, Gibco BRL) and incubated at room temperature for 5 minutes. One fifth volume of chloroform was added to the vial. It was then shaken vigorously for 15 seconds to mix and incubated at room temperature for 3 minutes. After a 5 minute centrifugation at 13 k rpms, the upper phase was collected and transferred to a new vial. 0.4 ml isopropanol was added to the vial. The mixture was incubated at room temperature for 10 minutes. To pellet the RNA, centrifugation was performed at 13 k rpms for 10 minutes. The supernatant was decanted, the RNA pellet washed with 75% EtOH and the centrifugation step was repeated. The supernatant was decanted and the RNA pellet was allowed to air dry for 15 minutes followed by suspension in RNase-free water. Spectrophotometry was performed to determine the concentration of RNA in the sample using the assumption that an $A_{260}$ reading of 1=40 μg/ml RNA when the $A_{260/280}$ is 1.7-2.0.

EXAMPLE 4

Northern Blot Analysis

A 1.1% agarose formaldehyde gel was cast. Five and ten micrograms of RNA were combined with denaturing buffer (final concentrations: 6% formaldehyde, 50% formamide and 0.1×MOPS) and heated to 65° C. for 10 minutes. A one-tenth volume of gel loading buffer was added and the sample was loaded onto the gel. Electrophoresis was performed at 75 volts in 1×MOPS buffer for ~3 hours. The gel was washed for 60 minutes in 10×SSC.

The RNA was transferred to a Hybond-N+nylon membrane (Amersham Biosciences, Piscataway, N.J.) by capillary action over 16 hours in 10×SSC. The RNA was then fixed to the nylon membrane by cross-linking using the Stratagene UV Stratalinker auto crosslink function (Stratagene, La. Jolla, Calif.). After fixing, the nylon membrane was allowed to air dry.

The Roche DIG High Prime DNA Labeling and Detection Kit I (Hoffmann-La Roche Ltd., Basel, Switzerland) was used to label 52 L1 wt and 52 L1 R DNA sequences with DIG to be used as probes to detect 52 L1 wt and 52 L1 R RNA on the Northern blot. The pre-hybridization, hybridization, and immunological development using an anti-DIG alkaline phosphatase-conjugated antibody were performed per the manufactures recommendations. Briefly, the blot was pre-hybridized at 37° C. for 30 minutes with gentle shaking. The probe was denatured by heating to 95° C. for 5 minutes and subsequent quenching on ice. The probe was added to the hybridization solution and applied to the membrane for 4 hours at 44.6° C. with gentle shaking. The hybridization solution was then removed and the blot was washed 2× for 5 minutes in 2×SSC with 0.1% SDS at room temperature, followed by an additional wash at 65° C. with 0.5×SSC and 0.1% SDS. The blot was then blocked for 30 minutes and anti-DIG alkaline phosphatase-conjugated antibody was applied at a 1:5000 dilation for 30 minutes. The blot was washed and the presence of probe-bound RNA was determined by NBT/BCIP substrate detection of the alkaline phosphatase conjugated anti-DIG bound antibody.

Initial analysis of yeast expressing HPV 52 μl wt suggested that HPV 52 L1 protein was expressed; however, the level was low. Northern blot analysis of RNA from yeast extracts of cultures induced to express HPV 52 L1 wt did not reveal any detectable HPV 52 μl RNA. Since some protein of the appropriate size was detected, it was clear that some full-length RNA transcripts were made. The HPV 52 L1 gene was rebuilt with yeast-preferred codon sequences and was engineered to omit any possible premature transcription termination sites to ensure robust transcription. Northern blot analysis of the HPV 52 L1 R transcript revealed that full-length transcripts were generated and detectable by Northern blot analysis (FIG. 3).

EXAMPLE 5

HPV 52 L1 Protein Expression

Frozen yeast cell pellets of galactose-induced cultures equivalent to $OD_{600}$=10 were thawed on ice and suspended in 300 μl of PC buffer (100 mM $Na_2HPO_4$ and 0.5 M NaCl, pH 7.0) with 2 mM PMSF. Acid-washed 0.5 mm glass beads were added at a concentration of ~0.5 g/tube. The tubes were vortexed for 3 cycles of 5 minutes at 4° C. with a 1 minute break. 7.5 μl of 20% TritonX100 was added and the vortex step was repeated for 5 minutes at 4° C. The tubes were placed on ice for 15 minutes, followed by centrifugation for 10 minutes at 4° C. The supernatant was transferred to a sterile microcentrifuge tube, which was labeled as total yeast protein extract, dated, and stored at −70° C.

EXAMPLE 6

Western Blot Analysis

Total yeast protein extract from twenty isolated yeast colonies for each HPV 52 L1 construct were analyzed by Western blot to confirm expression of HPV 52 L1 protein after galactose induction.

Ten, five, and two and one-half micrograms of total yeast protein extract were combined with SDS-PAGE loading buffer and heated to 95° C. for 10 minutes. The HPV 16 L1 protein, which is approximately 55 kDa, was included as a positive control, along with HPV L1-free total yeast protein extract as a negative control (data not shown). The proteins were loaded onto a 10% SDS-PAGE gel and electrophoresed in Tris-Glycine buffer. After protein separation, the proteins were Western-transferred from the gel to nitrocellulose and the resulting blot was blocked in 1× diluent buffer (Kirkegaard and Perry Laboratories, Gaithersburg, Md.) for 1 hour at room temperature with rocking. The blot was washed three times and yeast absorbed goat anti-trpE-HPV 31 L1 serum, which cross-reacts with HPV 16 and HPV 52 L1 proteins, was applied at room temperature for 16 hours. The blot was then washed three times and incubated with a 1:2500 dilution of anti-goat-HRP conjugated antibody for 1 hr. The blot was again washed three times and NBT/BCIP detection substrate was applied (Kirkegaard and Perry Laboratories). Immunoreactive proteins were detected as purple bands on the blot.

Figure 4:
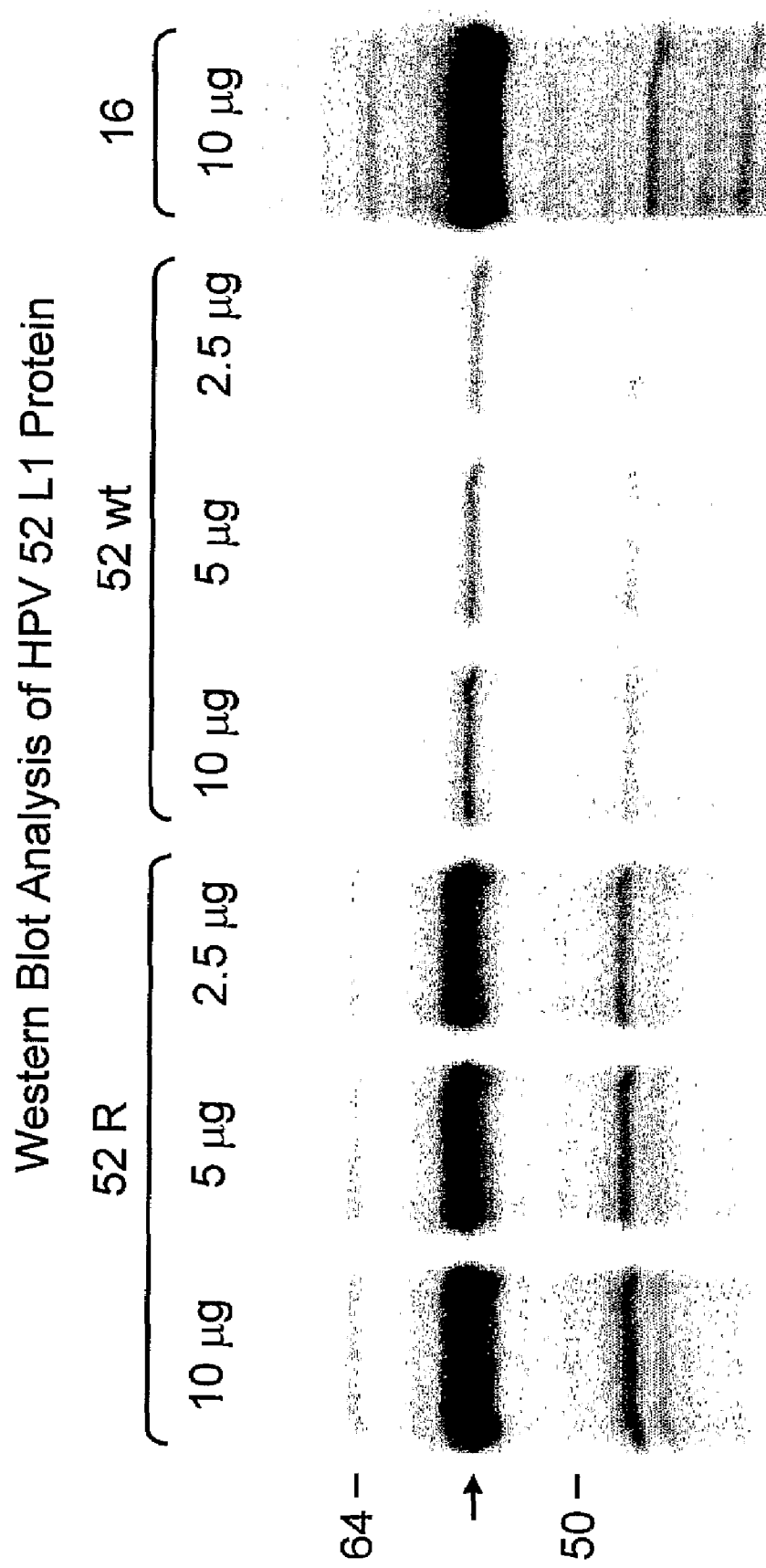
FIG. 4 shows a Western Blot of HPV 52 L1 wt (52 wt), and 52 L1 R (52R) proteins. HPV 16 L1 was included as a reference (16). Ten, five and two and one-half micrograms of total yeast protein extract were denatured and applied to a 10% SDS-PAGE gel. The protein was Western transferred. HPV 52 L1 protein was detected on the resulting blot using a yeast-absorbed anti-trpE-HPV 31 L1 goat polyclonal antiserum which cross-reacts with HPV 52 L1 and HPV 16 L1. Molecular weight markers are indicted in kDa on the left. The arrow indicates the position of the ~55 kDa HPV 52 L1 protein.

In all cases, the HPV 52 L1 protein was detected as a distinct immunoreactive band on the nitrocellulose corresponding to approximately 55 kDa. (FIG. 4) The intensity of the HPV 52 L1 R band (2.5 µg lane) appeared to be significantly greater than the HPV 52 L1 wt band (10 µg). It was clear that upon rebuilding, the expression level of codon-optimized HPV 52 L1 R increased more than four-fold, which is the limit of direct comparison on the Western blot.

EXAMPLE 7

Transmission Electron Microscopy

To demonstrate that the 52 L1 protein was in fact self-assembling to form pentameric-L1 capsomers, which in turn self-assemble into virus-like particles, a partially purified HPV 52 L1 R protein extract was subjected to transmission electron microscopy (TEM).

Yeast were grown under small scale fermentation and pelleted. The resulting pellets were subjected to purification treatments. Pellet and clarified yeast extracts were analyzed by immunoblot to demonstrate HPV 52 L1 protein expression and retention throughout the purification procedure. Clarified yeast extracts were then subjected to centrifugation over a 45%-sucrose cushion and the resulting pellet was suspended in buffer for analysis of HPV 52 L1 VLPs by TEM.

Figure 5:
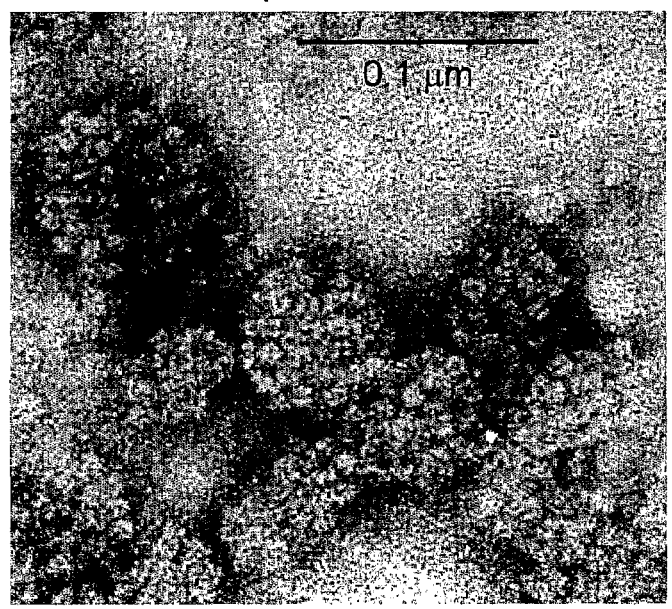
FIG. 5 shows a representative sample of HPV 52 VLPs composed of HPV 52 L1 R protein molecules, described herein, as visualized by transmission electron microscopy (see EXAMPLE 7). The diameter of the spherical particles in this crude sample ranged from between 40 and 70 nm with some particles displaying a regular array of capsomers. The bar represents approximately 0.1 µm.

A representative sample of the HPV 52 L1 R VLPs produced is shown in FIG. 5. The diameter of the spherical particles in this crude sample ranged from between 40 and 70 nm with some particles displaying a regular array of capsomers.

What is claimed is:

1. A nucleic acid molecule comprising a sequence of nucleotides that encodes an HPV52 L1 protein as set forth in SEQ ID NO:2, the nucleic acid sequence being codon-optimized for high-level expression in a yeast cell.

2. A vector comprising the nucleic acid molecule of claim 1.

3. A host cell comprising the vector of claim 2.

4. The host cell of claim 3, wherein the host cell is a yeast cell.

5. The host cell of claim 4, wherein the yeast cell is selected from the group consisting of: *Saccharomyces cerevisiae, Hansenula polymorpha, Pichia pastoris, Kluyveromyces fragilis, Kluyveromyces lactis,* and *Schizosaccharomyces pombe*.

6. The host cell of claim 4, wherein the host cell is *Saccharomyces cerevisiae*.

7. The nucleic acid molecule of claim 1, wherein the sequence of nucleotides comprises a sequence of nucleotides as set forth in SEQ ID NO:1.

* * * * *